(12) United States Patent
Bennarsten

(10) Patent No.: US 6,694,978 B1
(45) Date of Patent: Feb. 24, 2004

(54) HIGH-FREQUENCY OSCILLATION PATIENT VENTILLATOR SYSTEM

(75) Inventor: Johan Bennarsten, Gustavsberg (SE)

(73) Assignee: Siemens-Elema AB, Solna (SE)

( * ) Notice: Subject to any disclaimer, the term of this patent is extended or adjusted under 35 U.S.C. 154(b) by 45 days.

(21) Appl. No.: 09/708,637

(22) Filed: Nov. 9, 2000

(30) Foreign Application Priority Data

Dec. 2, 1999 (SE) .............................................. 9904382

(51) Int. Cl.[7] .............................................. A61M 16/00
(52) U.S. Cl. ........................... 128/204.21; 128/203.24; 128/203.25; 128/204.19; 128/207.17; 128/207.14
(58) Field of Search ....................... 128/203.24, 203.25, 128/204.21, 204.19, 207.17, 207.14, 203.12, 204.18; 600/525, 532, 533, 537, 538

(56) References Cited

U.S. PATENT DOCUMENTS

| | | | | |
|---|---|---|---|---|
| 2,918,917 A | * | 12/1959 | Emerson | 128/204.21 |
| 4,155,356 A | * | 5/1979 | Venegas | 128/204.23 |
| 4,215,681 A | * | 8/1980 | Zalkin et al. | 128/204.21 |
| 4,323,064 A | * | 4/1982 | Hoenig et al. | 128/202.22 |
| 4,495,947 A | | 1/1985 | Motycka | |
| 4,821,709 A | * | 4/1989 | Jensen | 128/204.21 |
| 4,838,259 A | | 6/1989 | Gluck et al. | |
| 5,044,362 A | * | 9/1991 | Younes | 128/204.21 |
| 5,165,398 A | | 11/1992 | Bird | |
| 5,307,794 A | * | 5/1994 | Rauterkus et al. | 128/200.24 |
| 5,494,028 A | * | 2/1996 | Devries et al. | 128/205.24 |
| 5,555,880 A | | 9/1996 | Winter et al. | |
| 5,611,335 A | * | 3/1997 | Makhoul et al. | 128/204.18 |
| 5,632,269 A | * | 5/1997 | Zdrojkowski | 128/204.21 |
| 5,692,497 A | * | 12/1997 | Schnitzer et al. | 128/204.18 |
| 5,704,346 A | | 1/1998 | Inoue | |
| 5,937,853 A | | 8/1999 | Ström | |
| 6,029,664 A | * | 2/2000 | Zdrojkowski et al. | 128/204.23 |
| 6,158,433 A | * | 12/2000 | Ong et al. | 128/204.21 |

FOREIGN PATENT DOCUMENTS

| | | |
|---|---|---|
| EP | 0 512 285 | 11/1992 |
| EP | 0 956 877 | 11/1999 |

* cited by examiner

Primary Examiner—Weilun Lo
Assistant Examiner—Michael Mendoza
(74) Attorney, Agent, or Firm—Schiff Hardin & Waite

(57) ABSTRACT

A patient ventilator system has a high-frequency oscillation ventilator connectable to a patient circuit and operable to induce oscillations within gas in the circuit at a predetermined high-frequency and a gas supply connectable to the patient circuit for supplying breathing gas thereto. A detection device is also included within the ventilator system and is adapted to monitor during the operation of the high-frequency oscillator ventilator, gas pressure and/or gas flow to detect a variation therein not derived from the induced high-frequency oscillations and to output a trigger signal dependent on the detected variation indicating a spontaneous breathing effort. The gas supply is operable on receipt of the trigger signal to supply breathing gas into the circuit at a level to assist the spontaneous breathing effort.

6 Claims, 1 Drawing Sheet

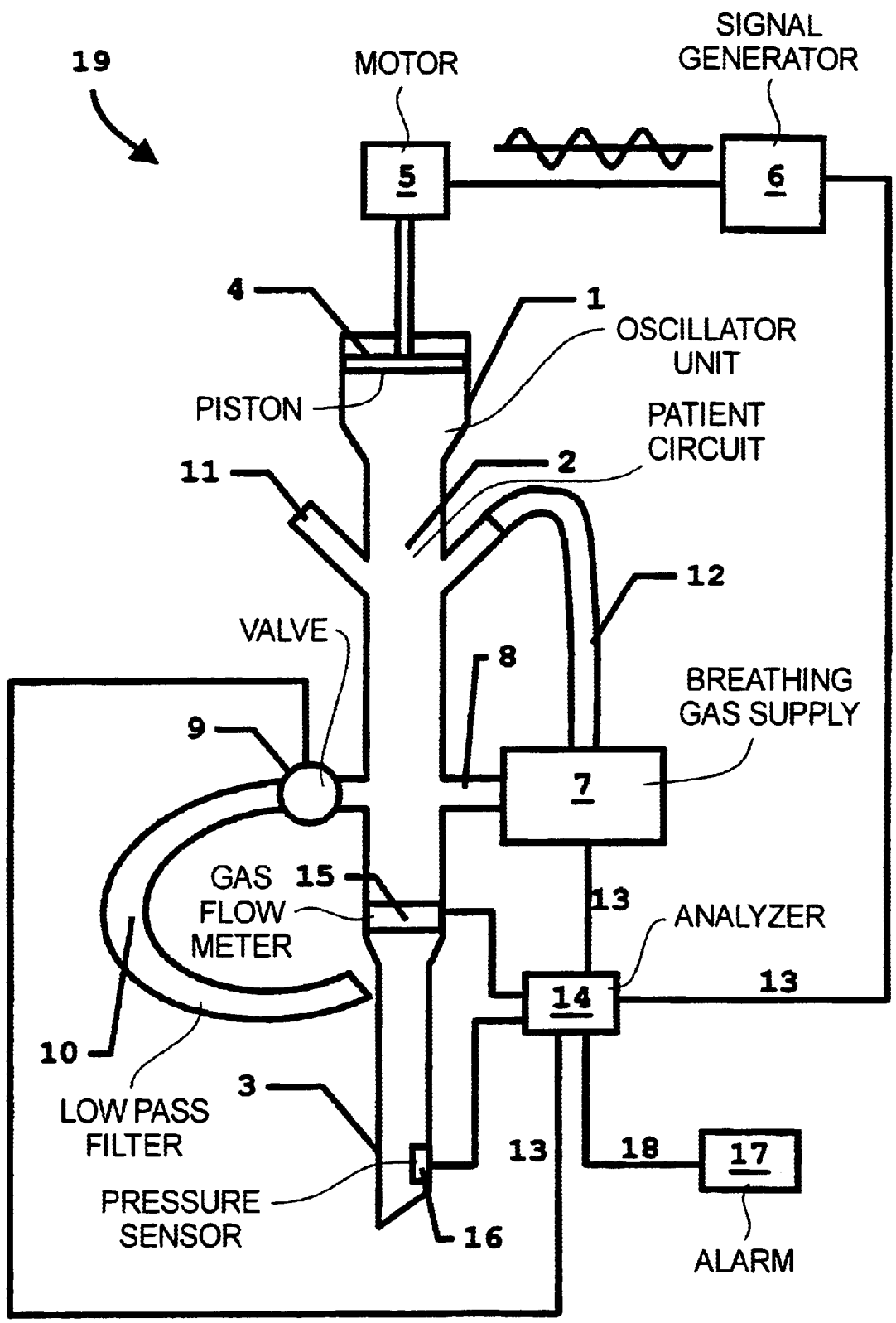

HIGH-FREQUENCY OSCILLATION PATIENT VENTILLATOR SYSTEM

BACKGROUND OF THE INVENTION

1. Field of the Invention

The present invention relates to a high-frequency oscillation (HFO) patient ventilator system, in particular to an HFO system capable of providing assisted ventilation support for a spontaneous breathing effort and also to a monitoring device capable of detecting a spontaneous breathing effort during HFO ventilation.

2. Description of the Prior Art

An HFO ventilator supplies breathing gas to the airways of a patient via a patient circuit at a frequency of approximately 150 breaths per minute or more and with tidal volumes significantly less than required during spontaneous breathing, typically at or below anatomical dead-space volumes. This is in marked contrast to a conventional mechanical ventilator which typically supplies breathing gas to the patient circuit at a frequency and with a tidal volume close to the values during spontaneous breathing.

HFO ventilators are well known and generally have an oscillator which is connectable in gas communication with one end of the gas tubing of a patient circuit. The circuit terminates in an opposite end, such as in an endotracheal tube, for connection to a patient's airways. The oscillator is then driven to vibrate a column of gas within the circuit to actively supply gas to and extract gas from the patient's airway. An HFO ventilator also has a gas supply for providing a constant, continuous so called 'bias' flow to the patient. This bias flow intersects the oscillatory pathway and serves to maintain (bias) an average positive airway pressure about which the high-frequency oscillations generated by the HFO ventilator occurs, as well as to wash exhaled gasses from the circuit. Gas leaves the circuit through an expiratory limb, which is designed as a low pass filter. The bias supply of such systems is usually insufficient to supply sufficient gas to a patient if the patient should attempt a spontaneous breath.

One known patient ventilator system, which reduces this problem is disclosed in U.S. Pat. No. 5,165,398. The system has an HFO ventilator and a conventional mechanical ventilator connected to a patient breathing circuit, and cooperable to provide, in one mode of operation, a conventional low frequency, large tidal, volume time cycled mechanical ventilator supply having superimposed thereon high-frequency oscillations from the HFO ventilator. In another mode of operation this system can act as an HFO ventilator with the conventional mechanical ventilator providing the continuous bias flow at a level to maintain a constant pressure. A mechanical pressure regulator is provided in the patient circuit proximal the patient end which operates to increase this continuous bias flow and maintain the pressure as a patient attempts to breath spontaneously. A non-assisted spontaneous breathing support mode of operation is thereby provided.

SUMMARY OF THE INVENTION

It is an object of the present invention to provide a breathing-assist system which is operable to provide high-frequency oscillation ventilation to a patient, but which is also able to provide sufficient breathing support to the patient if the patient should attempt a spontaneous breath.

This object is achieved in a first embodiment of the invention having a patient ventilator system capable providing assisted support of a spontaneous breathing effort detected during high-frequency oscillation ventilation. Thus, by monitoring for changes in one or both of the gas pressure and gas flow during the operation of an HFO ventilator which are unrelated to the high-frequency oscillations produced by that ventilator, a spontaneous breathing effort can be detected and a gas supply, preferably a conventional mechanical ventilator, can be operated to supply breathing gas at a level to assist the detected spontaneous breathing effort.

This object also is achieved in a second embodiment of the invention wherein a detection device is adapted to monitor for changes in one or both of the gas pressure and gas flow during the operation of an HFO ventilator which are unrelated to the high-frequency oscillations produced by that ventilator and to provide an output signal dependent on the monitored changes to indicate one or more of a spontaneous breathing effort, a leak and hyperinflation.

DESCRIPTION OF THE DRAWINGS

The figure is a schematic representation of a patient ventilator system according to the present invention connected to a patient circuit.

DESCRIPTION OF THE PREFERRED EMBODIMENTS

As shown in the figure, an oscillator unit 1 is connected to a patient circuit 2, which terminates at its opposite end in an endotracheal tube 3. A piston 4 is reciprocally movable within the oscillator unit 1 by a bidirectional motor 5. The motor 5 is driven in response to a variable frequency, variable period and amplitude wave drive pulse train (typically square or sine wave) output from a signal generator 6. The signal generator 6 is able to provide a pulse train typically as a continuous square or sine wave at variable frequency of approximately 3 Hz and above, to the motor 5 which then operates to reciprocate the piston 4 at that frequency. The generator 6 is also provided with controls to vary the amplitude of the pulse train, which in turn varies the stroke length of the piston 4, and to vary the duration of the positive and the negative going periods of the pulse train, which coincides with the inspiration to expiration ratio.

The piston 4 driven in this manner will, during each cycle of the drive pulse train, alternately produce a positive and a negative pressure in breathing gas within the circuit 2 relative to the static airway pressure of a patient who is connected to the circuit 2 with the endotracheal tube 3. This will cause breathing gas to be moved into and extracted from the patient's airways at a high-frequency determined by the output from the signal generator 6. A breathing gas supply 7 is also provided to supply a continuous bias flow through the conduit 8 to intersect the oscillating column of gas within the circuit 2 and exits through a valve 9 and a low pass filter 10. By controlling one or both of the bias flow rate and the opening of the valve 9 the static airway pressure can be maintained at a suitable level above ambient. The low pass filter 10 is designed to inhibit the escape of breathing gas from the system which carries the high-frequency oscillations induced by the movement of the piston 4. It will be appreciated by those skilled in the art that the above-described components cooperate to provide an example of a high-frequency oscillation (HFO) ventilator of the type generally known in the art and that the piston oscillator arrangement 1,4,5 may be replaced with other known means for inducing oscillations within the patient circuit 2,3 of a HFO ventilator such as a pneumatic oscillator or an electromagnetic oscillator (for example a speaker).

The gas supply 7, as well as providing the bias flow for the HFO ventilator, also operates as a conventional mechanical ventilator to supply breathing gas into the patient circuit 2 via conduit 12 in an amount substantially equivalent to that required during spontaneous breathing and at a pressure to cause substantial inflation of the patient's lungs. Switching of the gas supply 7 between bias supply and conventional mechanical ventilation is controlled by a trigger signal 13 from an analyzer 14, as is the operation of the valve 9 and the signal generator 6, as will be described below. The analyzer 14 is operably connected to receive output signals from a flow sensor 15 and pressure sensor 16, the latter being preferably located in use as close to the patient's airways as practicable—shown mounted at the open end of the endotracheal tube 3—so as to be better able to measure the small pressure changes induced by a spontaneous breathing effort. An optional alarm unit 17 may also be connected to receive a signal 18 from the analyzer 14 in the event of abnormal operating conditions of the ventilator system 19 being detected by the analyzer 14 and to provide a perceptible alarm signal dependent thereon.

In use the above-described patient ventilator system 19 operates by default as an HFO ventilator the output of which is controlled by the drive pulse train from the signal generator 6. When a spontaneous breathing effort by a patient is detected by the detection device (analyzer 14 and gas sensors 15,16) the analyzer 14 provides the trigger signal 13 which closes the valve 9, varies the output from the signal generator 6 to reduce or remove high-frequency oscillations from the gas in the circuit 2 and which switches the operating mode of the gas supply 7 to one of a conventional mechanical ventilator. In this mode the gas supply 7 functions to provide one of a time, pressure or volume controlled delivery of breathing gas to assist the detected spontaneous breathing effort of a patient. Such parametric delivery control in support of a patient breathing effort is well known in the art of conventional mechanical ventilation and is described for example, in U.S. Pat. No. 5,937,853, the contents of which are included herein by reference. The described gas supply 7 has a gas delivery unit and a regulating unit arranged to control the gas delivery unit to deliver gas to a patient according to prescribed parameter values. Sensors are disposed within the ventilator gas conduits to sense breathing efforts of the patient and to control the regulating unit in order to adapt gas delivery to deliver a pressure or volume support to the breathing effort of the patient to a predetermined total volume or pressure level. Such a ventilator is able to provide one of Pressure Supported Ventilation, Volume Supported Ventilation and Volume Supported Ventilation—Volume Controlled Ventilation in response to the sensed breathing effort.

The gas supply 7 continues to operate as a conventional mechanical ventilator to provide one or other of the support modes described above for a predetermined period of time after which it reverts to delivery of a bias flow through the conduit 8. The time period may be set, for example, within the gas supply 7 or within the analyzer 14. In the latter case a signal will be passed from the analyzer 14 to the gas supply 7, the valve 9 and the signal generator 6 to restore the HFO ventilator functions of these components 6,7,9. Alternatively these items 6,7,9 may be configured to operate the ventilator system 19 to provide conventional mechanical ventilation for as long as a trigger signal 13 is present so that in the latter case removal of the trigger signal 13 by the analyzer 14 after the predetermined period of time returns the ventilator system 19 to its default operation as an HFO ventilator. The predetermined period of time may be varied according to the frequency with which spontaneous breathing efforts are detected during HFO ventilation and the analyzer 14 may be further adapted to permanently switch the operating mode of the gas supply 7 to the one of conventional mechanical ventilator if the frequency of spontaneous breathing efforts increase above a threshold value set dependent on the clinical application of the ventilator system 19.

The example of the detection device according to the present invention shown in the figure has a separate flow meter 15 and a pressure sensor 16 (these may be provided as a unitary gas sensor providing both measurement functions) and an analyzer 14 which includes a suitably programmed microprocessor adapted to carry out the pressure and/or flow signal analysis described below in order to detect abnormal operating conditions of the ventilator system 19.

Average Periodic Pressure

This is defined herein as the average pressure proximal the patient's airways over one cycle of the high-frequency oscillations generated during high-frequency oscillation ventilation.

As a patient attempts to draw a breath (spontaneous breathing effort) the mean periodic pressure will reduce. The analyzer 14 can be adapted to detect a spontaneous breathing effort by monitoring the pressure detected by the sensor 16 during the operation of the HFO ventilator and calculating the mean periodic pressure. The analyzer 14 then operates to analyze the calculated average periodic pressure to determine when the calculated value falls below a pre-set value and to emit the trigger signal 13 indicating a detected spontaneous breathing effort.

A gas leakage within the ventilator system 19, however, would also result in a pressure reduction measured by the pressure sensor 16 and false detections of spontaneous breathing efforts by the analyzer 14. In order to reduce the occurrences of false detections, the analyzer 14 may be further adapted to carry out a time trend analysis of the calculated mean periodic pressure, i.e., to analyze the average periodic pressure to determine whether or not there is an increase in divergence of the calculated value from the trigger level over a number of cycles of the high-frequency oscillations. If this is so, this indicates that the pressure is continuing to decrease so that a spontaneous breathing effort is more likely than a leakage. Conversely, if a leakage is determined to be the more likely cause of the pressure reduction, the analyzer 14 may be adapted to provide the output signal 18 to the alarm 17.

Average Periodic Flow

This is defined herein as the average flow over one cycle of the high-frequency oscillations generated during high-frequency oscillation ventilation.

The average periodic flow depends on the inspiration to expiration ratio set by the waveform output from the signal generator 6 and for a 1:1 ratio the value of the average periodic flow will be zero. A spontaneous breathing effort will be characterized by an increased flow toward the patient. Thus the analyzer 14 may be adapted to monitor the pressure detected by the sensor 16 during the operation of the HFO ventilator and calculate the average periodic flow. The analyzer 14 is then further adapted to analyze the calculated average periodic flow to determine when the calculated value exceeds a threshold value (for example zero) and to emit the trigger signal 13 indicating a detected spontaneous breathing effort.

However, an increased flow toward the patient also may indicate a leakage or hyperinflation and lead to false detections of spontaneous breathing efforts by the analyzer 14. A pressure increase is associated with hyperinflation so by configuring the analyzer 14 to also monitor the pressure sensed by the pressure sensor 16 and to calculate the average periodic pressure therefrom false detections due to hyperinflation may be reduced. The analyzer 14 can then provide the trigger signal 13 to indicate a detection of a spontaneous breathing effort if there is determined to be both an increase in average periodic flow and no increase in average periodic pressure, or can emit the alarm signal 18 to indicate the presence of hyperinflation if the increase in flow is accompanied by an increase in pressure.

To further reduce the occurrence of false detection of spontaneous breathing efforts, a time trend analysis of the calculated average periodic pressure may be made to determine whether a leak is present and the trigger signal 13 or the alarm signal 18 provided also dependent on the time analysis, as discussed above.

Alternatively a time trend analysis of the calculated average periodic flow may be carried out by the analyzer 14 to determine whether the calculated value stabilizes over a number of periods. The trigger signal 13 will be output by the analyzer depending on the average periodic flow exceeding a trigger value and the presence of a continued increase of the mean flow, otherwise the alarm signal 18 may be provided.

Tidal Volume

The total amount of breathing gas (tidal volume) provided by the oscillating piston 4 during an inspiration phase (inspiratory tidal volume) and an expiration phase (expiratory tidal volume) of an oscillatory cycle during high-frequency oscillation ventilation can be analyzed within the analyzer 14 and a detection of a spontaneous breathing effort made based on this analysis. Knowledge of the duration of the positive and negative going periods of the drive pulse train output from the signal generator 6 allows the analyzer 14 to calculate the expected inspiration tidal volume and expiration tidal volume. In the event of a spontaneous breathing effort the inspiration tidal volume will increase and the expiration tidal volume remain constant or decrease, the net tidal volume will be possible and if a leakage is present the inspiration tidal volume will remain substantially constant and the expiration tidal volume decrease or remain constant and the net tidal volume will be zero. Adapting the analyzer 14 to monitor both tidal volumes will allow the analyzer 14 to detect a spontaneous breathing effort and differentiate this from a leakage.

In all configurations of the analyzer 14 needed to provide one or more of the above-described analysis information on the frequency and the duration of the positive and negative going periods of the drive pulse train, hence respectively the oscillating frequency of the gas within the circuit 2 and the inspiration to expiration ratio, may be manually entered into the analyzer 14 using an associated input device (not shown) such as a computer keyboard or a dedicated keypad, or may be passed to the analyzer 14 directly from a suitably adapted signal generator 6.

It will be appreciated by those skilled in the art that from the above discussion either the gas flow meter 15 or the pressure sensor 16 can be omitted from the detection device of the present invention, depending on the intended operation of the detection device. Moreover, it will be appreciated that the detection device of the present invention may be used to monitor for leakage and/or hyperinflation during the operation of a known HFO ventilator in addition or as an alternative to monitoring for a spontaneous breathing effort.

Although modifications and changes may be suggested by those skilled in the art, it is the intention of the inventor to embody within the patent warranted hereon all changes and modifications as reasonably and properly come within the scope of his contribution to the art.

I claim as my invention:

1. A breathing assist system comprising:
   a patient circuit adapted for connection to airways of a patient;
   a high-frequency oscillation ventilator connected to said patient circuit and operable to induce oscillations in gas in said circuit at a predetermined high frequency;
   a gas supply connected to the patient circuit for supplying breathing gas thereto;
   a detection device which monitors operation of the high-frequency oscillation ventilator comprising a gas sensor which produces an output signal representing at least one parameter selected from the group consisting of gas pressure and gas flow, said analyzer emitting and an analyzer which receives said output signal and which calculates from said output signal at least one average periodic value for said at least one parameter, a trigger signal dependent on a deviation of said calculated at least one average periodic value from an associated predetermined value indicating a spontaneous breathing effort; and
   said trigger signal being supplied from said analyzer to said gas supply and said gas supply, upon receipt of said trigger signal, supplying breathing gas to said circuit at a level to assist said spontaneous breathing effort.

2. A breathing assist system as claimed in claim 1 wherein said gas sensor is a pressure sensor and wherein said at least one parameter is gas pressure, and wherein said analyzer calculates an average periodic pressure value from said output signal, and wherein said analyzer calculates a change of said deviation of said average periodic pressure value from said associated predetermined value over a plurality of periods of said high-frequency oscillation, and emits said trigger signal dependent on said change.

3. A breathing assist system as claimed in claim 1 wherein said analyzer calculates a ratio of inspiratory tidal volume to expiratory tidal volume from said output signal, and emits said trigger signal dependent on said ratio.

4. A breathing assist system as claimed in claim 1 wherein said trigger signal is also supplied to said high-frequency oscillation ventilator and wherein said high-frequency oscillation ventilator is at least momentarily disenabled from producing said high-frequency oscillations upon receipt of said trigger signal.

5. A detection device for use with a high-frequency oscillation ventilator adapted for connection to a patient via a patient circuit, said detection device comprising:
   a gas sensor for sensing a parameter selected from the group consisting of gas pressure and gas flow in said patient circuit, and which produces a sensor output representing said parameter; and
   an analyzer supplied with said sensor output for analyzing said sensor output to detect a variation therein which does not arise from oscillations induced by said ventilator at a predetermined high-frequency, said analyzer receiving said output signal and calculating from said output signal at least one average periodic value for said at least one parameter, and emitting a trigger signal dependent on a deviation of said calculated at least one average periodic value from an associated predetermined value, indicating a spontaneous breathing effort.

6. A detection device as claimed in claim 5 wherein said analyzer identifies a change in said deviation of said at least one average periodic value from said associated predetermined value over a plurality of periods of said predetermined high-frequency and which generates said output signal dependent on said change.

\* \* \* \* \*